United States Patent [19]

Fu et al.

[11] Patent Number: 5,502,222
[45] Date of Patent: Mar. 26, 1996

[54] PROCESS FOR PREPARING DELTA 9,11 AND 21-CHLORO CORTICOSTEROIDS

[75] Inventors: Xiaoyong Fu; Tiruvettipuram K. Thiruvengadam, both of Edison; Chou-Hong Tann, Elizabeth; Junning Lee, Gillette; Cesar Colon, Rahway, all of N.J.

[73] Assignee: Schering Corporation, Kenilworth, N.J.

[21] Appl. No.: 252,302

[22] Filed: Jun. 1, 1994

[51] Int. Cl.$^6$ .................. C07J 5/00; C07J 7/00; C07J 75/00

[52] U.S. Cl. .......................... 552/595; 552/596

[58] Field of Search ..................... 552/595, 596

[56] References Cited

U.S. PATENT DOCUMENTS

| Re. 28,369 | 3/1975 | Arth et al. | 260/397 |
|---|---|---|---|
| 3,284,477 | 11/1966 | Rausser et al. | |
| 3,639,434 | 2/1972 | Oxley et al. | 260/397 |
| 3,933,799 | 1/1976 | Phillipps | 260/239 |
| 3,947,409 | 3/1976 | Hirschmann . | |

FOREIGN PATENT DOCUMENTS

| 003341 | 8/1979 | European Pat. Off. . |
| WO88/09337 | 12/1988 | WIPO . |

OTHER PUBLICATIONS

Wuts, et al., *Syn. Comm.*, 23 (No. 15) 2199–221 (1993).
Rausser, et al., *J. Org. Chem.*, 31, (No. 1) 26–31 (1966).
Ayer, *Tetr. Lett.*, (No. 23) 1065–1069 (1962).
Oliveto, et al., *J. Amer. Chem. Soc.*, 80, (No. 16) 4431 (1958).

*Primary Examiner*—Kimberly J. Kestler
*Attorney, Agent, or Firm*—Paul A. Thompson

[57] ABSTRACT

Described is a process for the regioselective dehydration of 11-hydroxy steroids using $PCl_5$, $PCl_3$, $POCl_3$ or either $SOCl_2$ and imidazole, or $PPh_3$ and $CCl_4$. The disclosed process selectively forms $\Delta^{9,11}$ steroids from either 11-α- or 11-β-hydroxy steroids, and can also be used for the one-step conversion of 11,21-dihydroxy steroids to 21-chloro-$\Delta^{9,11}$ steroids.

5 Claims, No Drawings

PROCESS FOR PREPARING DELTA 9,11 AND 21-CHLORO CORTICOSTEROIDS

BACKGROUND OF THE INVENTION

The synthesis of corticosteroids having therapeutic utility, such as mometasone, betamethasone and beclomethasone, requires functionalization of the C-9 and C-11 positions of the steroid molecule. The functionality is generally introduced via $\Delta^{9,11}$ steroid intermediates.

Methods for preparing steroids having a 9,11 double bond are known in the art. For example, an 11-hydroxy steroid can be converted to the corresponding mesylate (by treating with mesyl chloride) which is transformed into a $\Delta^{9,11}$ steroid via an elimination reaction. However, the prior art methods are not regiospecific in the case of 11α-hydroxy steroids and typically lead to mixtures of $\Delta^{9,11}$ steroid containing 10–15% of the analogous $\Delta^{11,12}$ steroids. Separation of these regio-isomeric products is difficult, generally requiring laborious physical separation procedures, resulting in increased costs and lower yields. It would therefore be desirable to develop an efficient regioselective method for preparing $\Delta^{9,11}$ steroids, from either 11α- or 11β-hydroxy steroids, for use as intermediates in the synthesis of corticosteroids.

The introduction of a 21-chloro group is also of commercial importance, e.g. for preparing intermediates and therapeutically important compounds such as mometasone. The conversion of 21-hydroxy steroids to the analogous 21-chloro steroid by chloride displacement of a 21-methanesulfonyl intermediate is known. However, this reaction is not regioselective in the case of 11-hydroxy steroids, as methanesulfonyl chloride reacts with both the 11- and 21-hydroxy groups. In addition, Wuts, et al., *Syn. Comm.*, 23, (15) 2199–2211 (1993) describes a method for preparing 21-chloro steroids using the Vilsmeier reagent (prepared from DMF and POCl₃ or phosgene).

In view of the importance of both 21-chloro groups and 9,11-double bonds it would be desirable to develop a one-step process for efficiently introducing both functional groups in a single steroid molecule.

SUMMARY OF THE INVENTION

The present invention provides a regioselective process for preparing $\Delta^{9,11}$ steroids of the formula I

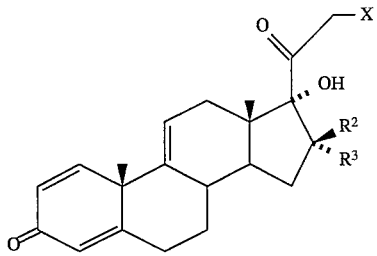

wherein: one of $R^2$ or $R^3$ is $CH_3$ and the other is H; and X is H, halogeno or —OR, wherein R is H or —C(O)R¹, and R¹ is $CF_3$, $C_1$–$C_6$ alkyl or $C_1$–$C_6$ alkoxy.

The process of the present invention is chemically efficient, and where a $\Delta^{9,11}$ group and a 21-chloro group are required, allows the one step introduction of both functional groups.

The instantly claimed process comprises treating an 11-α-hydroxy steroid of the formula II or an 11-β-hydroxy steroid of the formula IV

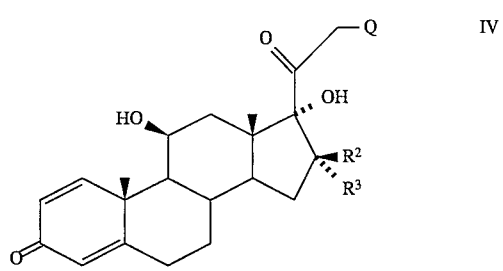

wherein Q is —OSO₂C₆H₄CH₃, —OSO₂CH₃, —O—C(O)O—B or X, wherein B is a group of the formula

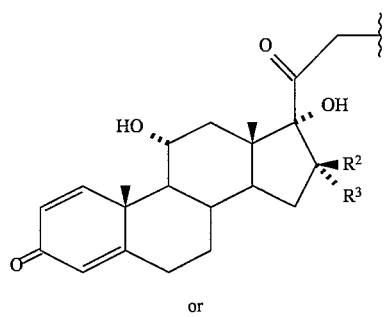

or

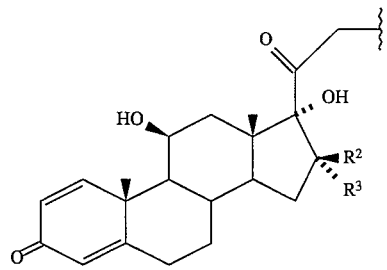

and wherein X, $R^2$ and $R^3$ are as defined above, with PCl₅, PCl₃, POCl₃ or either SO₂Cl₂ and imidazole, or PPh₃ and CCl₄, to form a compound of the formula I.

The present invention also provides a process for regioselectively preparing a 21-chloro steroid of the formula

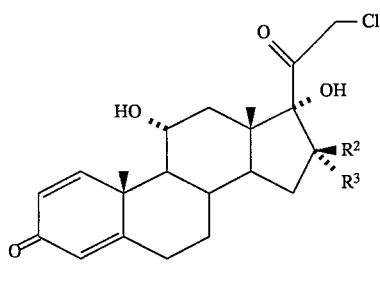

or

-continued

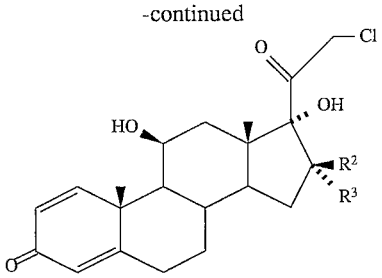

wherein one of $R^2$ or $R^3$ is $CH_3$ and the other is H, comprising treating a triol of the formula

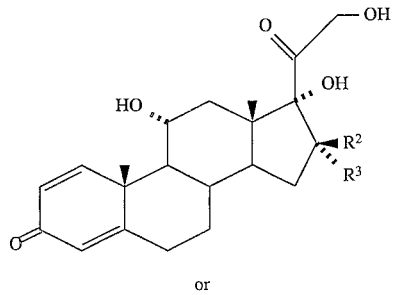

or

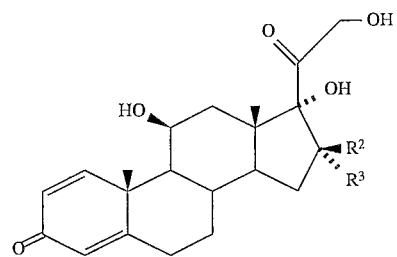

wherein $R^2$ and $R^3$ are as defined above, with either triphenylphosphine and $CCl_4$ or p-tolueneslfonyl chloride and LiCl.

In an alternative embodiment the present invention further provides a process for preparing $\Delta^{9,11}$ steroids of the formula I, wherein X, $R^2$ and $R^3$ are as defined above, comprising heating an 11-β-chloro steroid of the formula III

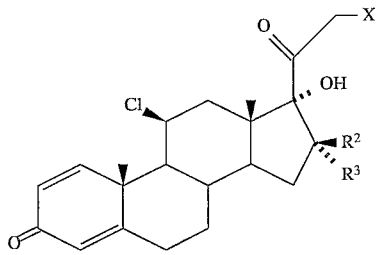

wherein X, $R^2$ and $R^3$ are as defined above, in the presence of a polar solvent to form a compound of the formula I. Preferably the polar solvent is DMSO, DMF or a mixture of $CH_3CN$ and water, diglyme and water, or dioxane and water.

DETAILED DESCRIPTION

As used herein, the term "alkyl" means a straight or branched unsaturated hydrocarbon chain having from 1 to 6 carbon atoms and "alkoxy" similarly refers to an alkoxy group having from 1 to 6 carbon atoms;

"halogeno" means bromo, chloro or iodo;

"Tertiary amine base" means pyridine or a trialkylamine such as triethylamine, N-ethylpiperidine, DMAP or Hünigs base, or combinations thereof.

The following solvents and reagents employed in the process of the present invention are identified by the abbreviations indicated: ethyl acetate (EtOAc); acetic acid (HOAc); tetrahydrofuran (THF); dimethylsulfoxide (DMSO); triethylamine ($Et_3N$); diisopropylethylamine (Hünigs base); methanol (MeOH); 1,8-diazabicyclo[5.4.0]undec-7-ene (DBU); triphenylphosphine ($PPh_3$); diisopropyl ether ($iPr_2O$); dimethoxyethane (DME); t-butylmethyl ether (t-BuOMe); N,N-dimethylaminopyridine (DMAP); dimethylformamide (DMF); p-toluenesulfonyl chloride (TsCl).

The present invention comprises a process, designated Process A, for regio-selectively dehydrating an 11-hydroxy steroid of the formula II or IV to form a $\Delta^{9,11}$ steroid of the formula I, as shown in Reaction Scheme A.

Reaction Scheme A

Step A1(a)

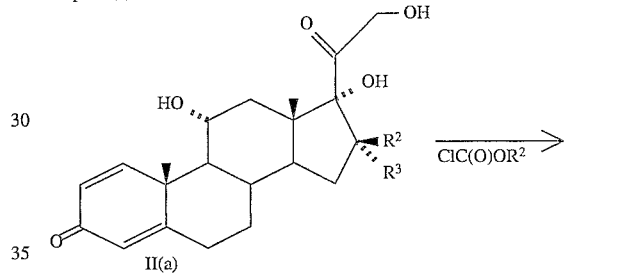

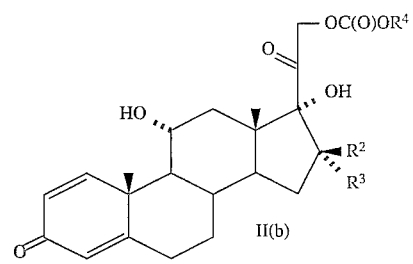

Step A1(b)

II(a) $\xrightarrow{R^4C(O)L}$

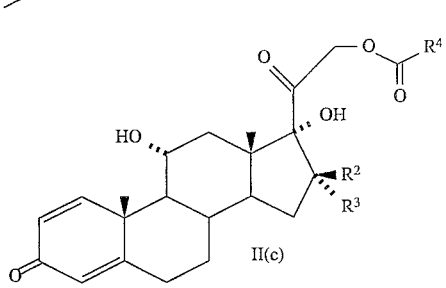

Step A1(c)

II(a) $\xrightarrow{ClSO_2R^5}$

-continued
Reaction Scheme A

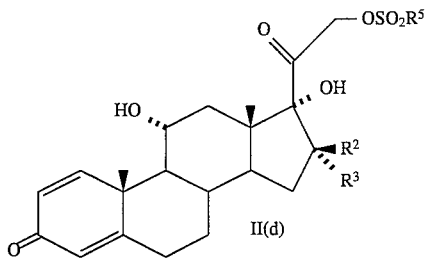

II(d)

Step A2
II(a) or II(b) or
II(c) or II(d) or

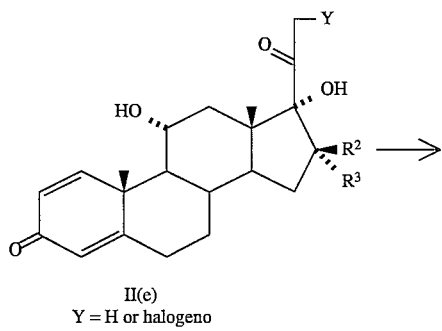

II(e)
Y = H or halogeno

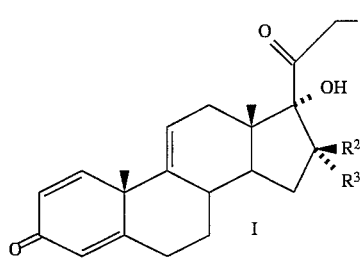

I

In Step A1(a) an 11-hydroxy steroid II(a), e.g. a compound of formula II wherein X is —OR and R is H, is treated with an alkylchloroformate of the formula $ClCO_2R^4$, where $R^4$ is $C_1$–$C_6$ alkyl, preferably ethylchloroformate, and a tertiary amine base, preferably N-ethylpiperidine, Hünigs base or $Et_3N$, to form a compound of formula II(b), e.g. a compound of the formula II wherein Q is or X or —O—C(O)O—B, wherein B is as defined above, X is —OR, R is —C(O)R$^1$ and R$^1$ is $C_1$–$C_6$ alkoxy.

Alternatively, in Step A1(b) compound II(a) is treated with $(CF_3CO)_2O$ or an acylating agent of the formula $R^4C(O)L$, wherein $R^4$ is as defined above and L is a suitable leaving group such as halogeno, and a tertiary amine base, such as pyridine, optionally in the presence of DMAP, to form a compound of the formula II(c), e.g. a compound of the formula II wherein Q is X, X is —OR, R is —C(O)R$^1$ and R$^1$ is $CF_3$ or $C_1$–$C_6$ alkyl.

In a second alternative, shown above as Step A1(c), compound II(a) is treated with a sulfonyl chloride of the formula $ClSO_2R^5$, wherein $R^5$ is —$C_6H_4CH_3$, in the presence of a tertiary amine base, preferably $Et_3N$, DMAP or a mixture of $Et_3N$ and DMAP, at $-20°$ to $60°$ C., preferably at $0°$ to $40°$ C., and most preferably at $10°$ to $30°$ C., to form a compound of the formula II(d), e.g. a compound of the formula II wherein Q is X, X is —$OSO_2$ R$^5$ and R$^5$ is —$C_6H_4CH_3$.

In Step A2, a compound of the formula II(e), e.g. a compound of the formula II wherein Q is X and X is H or halogeno, or a compound of the formula II(a), II(b), II(c) or II(d), is treated with $PCl_5$, $PCl_3$, $POCl_3$ or either $SO_2Cl_2$ and imidazole, or $PPh_3$ and $CCl_4$. Where the reaction is carried out using $PCl_5$, it is preferably run at low temperature, e.g. at $0°$ to $-100°$ C., preferably at $-40°$ to $-90°$ C., and most preferably at about $-60°$ C. to $-85°$ C., in a suitable organic solvent such as THF, to form a $\Delta^{9,11}$ steroid of the formula I.

Where Step A2 is carried out using $PPh_3$ and $CCl_4$, the reaction is run at $0°$ to $100°$ C., preferably at $20°$ to $80°$ C., in a suitable solvent, such as $CH_3CN$. Where $SO_2Cl_2$ and imidazole are used in Step A2, the reaction is carried out in a suitable solvent, such as THF, at $0°$ to $-100°$ C., preferably about $-10°$ to $-80°$ C., and most preferably at $-20°$ to $-78°$ C. Finally, where $POCl_3$ is used, Step A2 is carried out in the presence of pyridine in a suitable solvent, such as $CH_2Cl_2$, at $-40°$ to $100°$ C., preferably at $-20°$ to $80°$ C., and most preferably at $-5°$ to $60°$ C. When $PCl_3$ is used in Step A2, the reaction is preferably carried out at $-80°$ to $50°$ C., preferably at $-40°$ to $30°$ C., and most preferably at $-20°$ to $25°$ C.

Compounds of the formula I wherein X is —OR and R is —C(O)R$^1$ can be converted to compounds of the formula I wherein X is —OR, and R is H, by hydrolysis using known methods. In addition, compounds of the formula I wherein X is —OR, and R is H, can be converted to compounds of the formula I wherein X is halogeno, via known methods.

The present invention further comprises Process A as shown above wherein the analogous 11-β-hydroxy steroid, e.g. a compound of the formula IV, is used in place of the 11-α-hydroxy steroid (II).

Starting compounds of the formula II(a) and II(e), and the analogous compounds of the formula IV are known and can be prepared by established methods.

The $\Delta^{9,11}$ steroids prepared by the Process A of the present invention are of high purity and preferably contain less than 2% of the unwanted $\Delta^{11,12}$ regio-isomers.

The present invention also comprises a process for regioselectively converting an 11,17,21-trihydroxy steroid to a 21-chloro-11,17-dihydroxy steroid as shown in Reaction Scheme AA.

Reaction Scheme AA

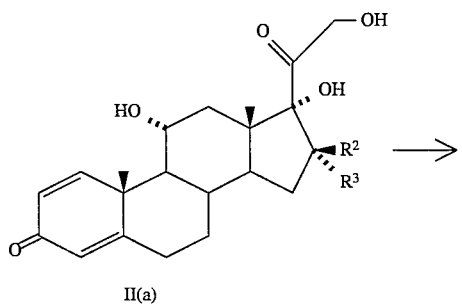

II(a)

-continued
Reaction Scheme AA

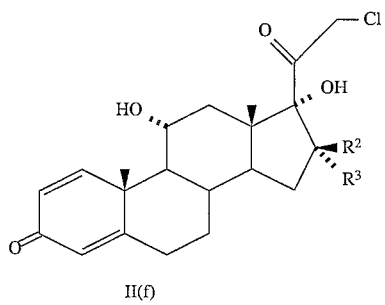

II(f)

In Reaction Scheme AA, a compound of the formula II(a) is treated with $PPh_3$ and $CCl_4$ in the presence of a suitable solvent, such as $CH_3CN$, at $-20°$ to $40°$ C., preferably at $0°$ to $30°$ C., and most preferably at $20°$ to $30°$ C., to selectively form a compound of the formula II(f), i.e., a compound of the formula II wherein Q is X and X is Cl.

Alternatively, in Reaction Scheme AA, a compound of the formula II(a) is treated with TsCl and a tertiary amine base, such as $Et_3N$ or a combination of $Et_3N$ and DMAP, in a suitable sovent, such as $CH_2CH_2$, at $-20°$ to $40°$ C., preferably at $0°$ to $30°$ C., and most preferably at about room temperature, to form a 21-tosylate intermediate, which is then treated with LiCl at $20°$ to $60°$, preferably at $30°$ to $50°$ and most preferably at about $40°$ C., to form the 21-chloride II(f).

The present invention further provides a Process AA as shown above wherein the analogous 11-β-hydroxy steroid, e.g. a compound of the formula IV, is used in place of the 11-α-hydroxy steroid II(a).

In an alternative embodiment, the present invention comprises a process, designated Process B, for regio-selectively converting an 11-β-chloro steroid of the formula III to form a $\Delta^{9,11}$ steroid of the formula I, as shown in Reaction Scheme B.

Reaction Scheme B

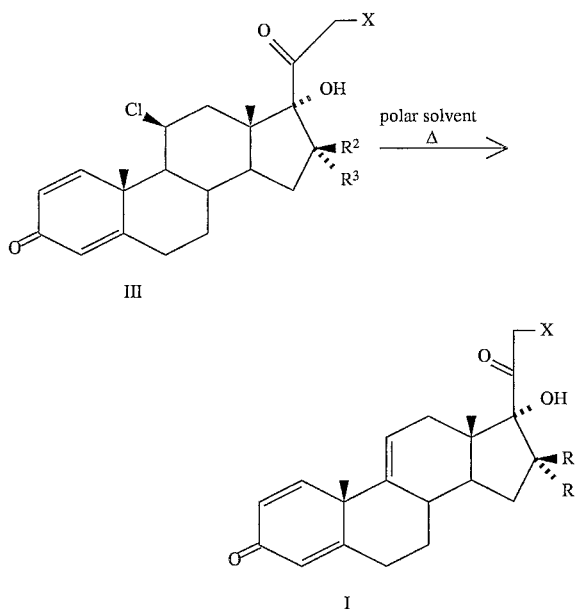

In Reaction Scheme B a compound of the formula III is combined with a suitable polar solvent, preferably DMSO, DMF or a mixture of $CH_3CN$ and water, diglyme and water, or dioxane and water. The reaction is generally carried out at $20°$ to $150°$ C. Typically for compounds III wherein X is —OR and R is H, the reaction is preferably carried out at $20°$ to $80°$, and most preferably at $30°$ to $50°$ C., while for compounds III where X is H, halogeno or —OR wherein R is —$C(O)R^1$, the reaction is preferably carried out at $50°$ to $150°$ C., more preferably at $80°$ to $120°$ C., and most preferably at $90°$ to $110°$ C., to form a compound of formula I.

Chloro substituted steroids of the formula III can be prepared by established methods. For example, treating a steroid of the formula II with a chlorinating agent, such as $PCl_3$, $PCl_5$/pyridine, or $CCl_4/PPh_3$, provides the 11-β-chloro steroid III. Compounds of the formula II are known and can be prepared via methods disclosed in the prior art.

The following preparations and examples are illustrative of the process of the present invention.

GENERAL METHODS

The ratios of $\Delta^{9,11}$ to $\Delta^{11,12}$ steroids, and the percentages of $\Delta^{9,11}$, $\Delta^{11,12}$ and 11-β-chloro steroids, presented in the Examples below were determined via HPLC analysis (μ-Bondapak® C-18 column, 1:1 $CH_3CN/H_2O$, 1–2 mL/min., U.V. detector at 254 nm) of the products.

Molar yields are based on the quantity of starting compound and product, corrected for starting compound and product purity, as determined by HPLC using the above conditions.

PREPARATION 1

PREPARATION 1

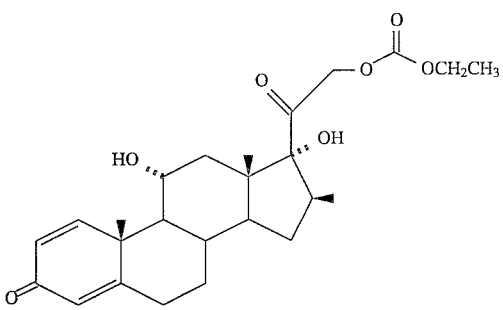

Combine 20.0 g of 16β-methyl-11α,17α, 21-trihydroxypregna-1,4-diene-3,20-dione, 80 mL of $CH_2Cl_2$ and 30 mL of $Et_3N$. Stir the mixture, cool to $-15°$ to $-10°$ C. and slowly add a solution of 6.5 mL of $ClCO_2CH_2CH_3$ in 10 mL of $CH_2Cl_2$ over a period of 1 h, while maintaining the temperature at $-15°$ to $-10°$ C. Stir the mixture at $-15°$ to $-10°$ C. for 30 min, then warm to $20°$ to $25°$ C. and stir for 2 to 4 h more. Add 40 mL of THF and 80 mL of water, then stir at $20°$ to $25°$ C. while slowly adding 13 mL of concentrated HCl to adjust the pH to 2. Stir for 15 min more then recheck the pH. (If the pH is >2 then add HCl to adjust to pH 2 and stir 30 min more.) Allow the mixture to settle and separate the layers. Extract the aqueous layer with 50 mL of $CH_2Cl_2$, combine the extract with the original organic layer and heat the combined organic solution to distill to a volume of 40 mL. Cool the concentrated solution, add 40 mL of THF, then heat again to distill to a volume of 40 mL. Cool to give a solution of the title compound for use in Example 1.

Alternatively, the title compound can be isolated from the product solution, e.g. by concentration in vacuo, and if necessary purified.

PREPARATION 1A

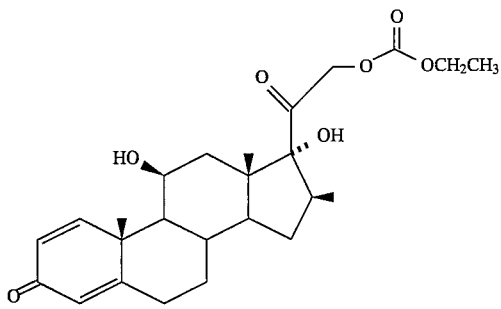

The title compound is prepared by treating a mixture of 0.050 g of 16β-methyl-11β,17α, 21-trihydroxypregna-1,4-diene-3,20-dione, 2 mL of CH$_2$Cl$_2$ and 0.1 mL of Et$_3$N, with 0.5 mL of a solution of 0.3 mL of ClCO$_2$CH$_2$CH$_3$ in 10 mL of CH$_2$Cl$_2$ via essentially the same procedure as described for Preparation 1.

PREPARATION 1B

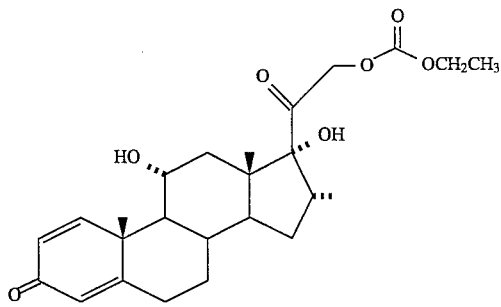

The title compound is prepared by treating a mixture of 2 g of 16α-methyl-11α,17α, 21-trihydroxypregna-1,4-diene-3,20-dione, 15 mL of CH$_2$Cl$_2$ and 3 mL of Et$_3$N, with a solution of 0.65 mL of ClCO$_2$CH$_2$CH$_3$ in 2 mL of CH$_2$Cl$_2$ via essentially the same procedure as described for Preparation 1.

PREPARATION 2

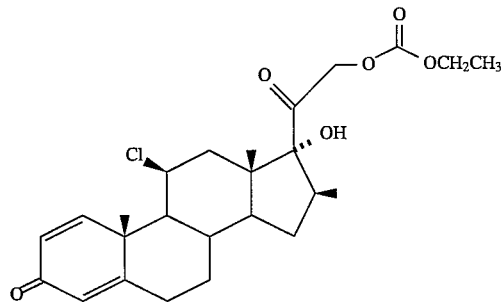

Combine 2 g of the isolated product of Preparation 1 with 30 mL of CH$_2$Cl$_2$ and 6 mL of pyridine. Add an excess of PCl$_5$ and stir the mixture at room temperature for 30 min. Quench the reaction mixture by adding water, then dilute with 100 mL of CH$_2$Cl$_2$. Wash the resulting solution with 50 mL of 6N HCl (aqueous), separate the organic and aqueous layers, and extract the aqueous layer with CH$_2$Cl$_2$ (2×50 mL). Combine the organic solutions, wash successively with 1N HCl (aqueous), water and brine, then dry over Na$_2$SO$_4$. Concentrate the organic solution in vacuo to a residue, then purify the residue by chromatography (silica gel, 30/70 then 50/50 EtOAc/hexane) to give 0.15 g of the title compound. $^1$H NMR (CDCl$_3$): 7.20 (d, J=10 Hz); 6.28 (d, J=10 Hz); 5.97 (s); 4.98 (d, J=18 Hz); 4.85 (d, J=18 Hz); 4.62 (br. s); 4.21 (q, J=7 Hz); 2.6–2.0 (m); 1.5 (s); 1.31 (t, J=7 Hz); 1.15 (d, J=7 Hz); 1.1 (s). Mass Spectrum (FAB): (M$^+$+3) 467; (M$^+$+1) 465; (M$^+$+1-HCl) 429.

Alternatively, the 11-β-chloro steroid is prepared by treating a solution of the product of Preparation 1 in THF with 2 equiv. of PCl$_3$ under substantially the same conditions as described above for 4.5 h. The title compound is then isolated as described above.

PREPARATION 3

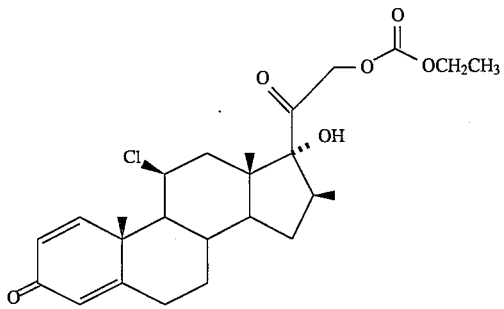

Combine 1 g of the isolated product of Preparation 1 with 10 mL of THF and 5 mL of CCl$_4$. Add 1 g of PPh$_3$ and stir the mixture at 70° C. for 1 h. The product is isolated via substantially the same procedure as described for Preparation 2 to give the title compound.

PREPARATION 4

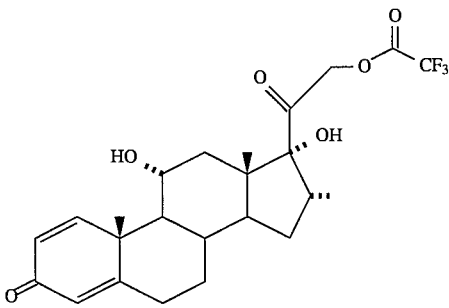

Cool 2 g of 16α-methyl-11α,17α, 21-trihydroxy-pregna-1,4-diene-3,20-dione to −20° C. Add 15 mL of THF then slowly add (at a rate of 0.2 mL/min) a solution of 0.8 mL of (CF$_3$CO)$_2$O in 5 mL of THF and stir the mixture at −20° C. Add another 0.05 mL of (CF$_3$CO)$_2$O in 1 mL of THF and stir at −20° C. to give a solution of the trifluoroacetyl ester product.

PREPARATION 5

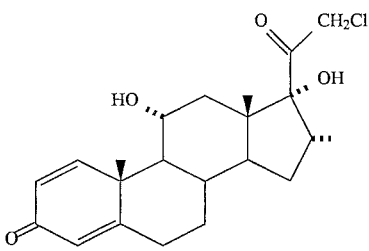

Combine 2 g of 16α-methyl-11α,17α, 21-trihydroxypregna-1,4-diene-3,20-dione, 34 mg (0.05 equivalents) of DMAP, 14 mL of $CH_2Cl_2$, 3 mL of $Et_3N$ and 1.21 g of TsCl. Stir the mixture at room temperature for 1 h, then add 1 mL of MeOH and stir for 30 min. Add 1 g of LiCl and heat the mixture to 40° C. for 2.5 h. Filter and wash with $CH_2Cl_2$ (2×15 mL). Combine the $CH_2Cl_2$ washes, wash with $NaHCO_3$ and dry over $Na_2SO_4$. Concentrate in vacuo to give the 21-chloride product.

EXAMPLE 1

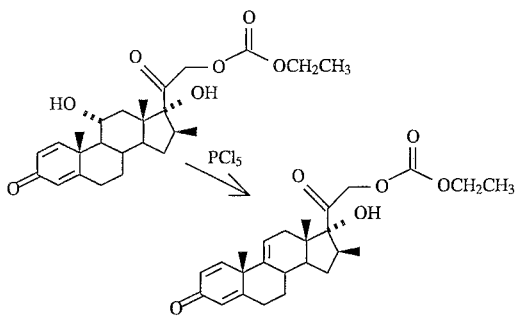

Dilute the 40 mL product solution from Preparation 1 with 100 mL of THF and cool to −85° to −83° C. Slowly add 20 g of $PCl_5$ (over a 30 min. period), while keeping the reaction temperature at −85° to −83° C. After 30 to 90 min., slowly pour the mixture into 800 mL of stirred water (at 10° to 15° C.). Stir the mixture at 10° to 15° C. for 30 min., then slowly add 32 mL of 50% NaOH (aqueous) to adjust to pH 7.5. Allow the mixture to stand at 10° to 15° C. for 30 min., then filter and wash the solids with 3×200 mL of water. Dry the solids in a vacuum oven at 60° C. overnight to give the triene product (92% overall yield from the starting trihydroxypregnadienedione of Preparation 1).

EXAMPLE 2

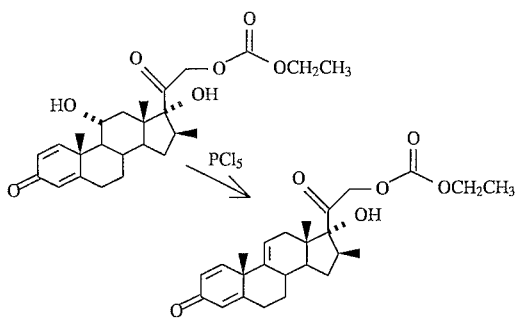

Combine 10 g of the 11-α-hydroxy steroid (isolated from the product solution of Preparation 1) and 65 mL of THF. Stir the mixture at room temperature to dissolve the steroid, then cool to −78° C. Add 8 g of $PCl_5$ in small portions over a period of 30 min. while maintaining the temperature below −73° C. Stir the mixture at −78° C. for 30 min., then add the mixture to 400 mL of water and stir for 30 min. at room temperature. Filter and wash the solids with 300 mL of water. Dry the solid under vacuum at 60° C. overnight to give 9.33 g of the title compound (94.5% molar yield). The ratio of $\Delta^{9,11}$ to $\Delta^{11,12}$ steroid is 98:2.

Using the solvent and temperature indicated, and otherwise substantially the same procedure as described above, the following results were obtained:

| Solvent | Reaction Temp. | % $\Delta^{9,11}$ | % $\Delta^{11,12}$ | % 11β-Cl | Comment |
|---|---|---|---|---|---|
| $CH_2Cl_2$/pyridine | room temp. | 70.4 | 11.2 | 18.4 | |
| pyridine | room temp. | 52.3 | 3.8 | 43.9 | |
| $CH_2Cl_2$ | −20° C. | 74.4 | 14.6 | 11.0 | |
| EtOAc | −20° C. | 80.2 | 17.9 | 1.9 | |
| t-BuOMe | −45° C. | 95.7 | 4.3 | — | 80% sm[1] after 2 h |
| DME | −45° C. | 81.4 | 18.6 | — | |
| dioxane | room temp, | 55.1 | 7.4 | 37.5 | |
| i-$Pr_2O$ | −30° C. | 94.0 | 6.0 | — | 85% sm[1] after 0.5 h |
| toluene | −45° C. | 95.0 | 5.0 | — | 50% sm[1] after 2 h |
| $CH_3CN$ | room temp. | 82.8 | 1.8 | 3.1 | (a) |
| THF | room temp. | 81.1 | 7.6 | 11.3 | |
| THF | −20° C. | 92.3 | 4.9 | 2.8 | |
| THF | −45° C. | 95.5 | 3.3 | 1.2 | |
| THF | −78° C. | 97.5 | 1.8 | 0.7 | |
| THF | −85° C. | 98.4 | 1.3 | 0.3 | |

[1]sm = unreacted starting material
(a) impurities were detected

EXAMPLE 3

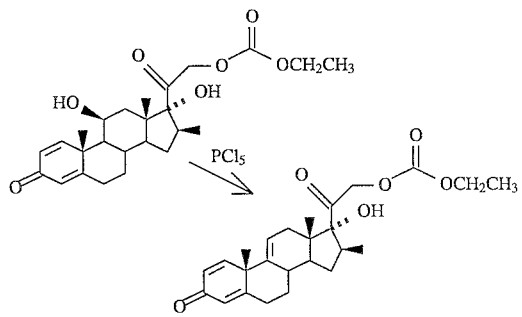

Combine the 11-β-hydroxy steroid of Preparation 1A and 5 mL of THF. Cool to −78° C., add 0.1 g of $PCl_5$ and stir at −78° C. for 1 h. Add 0.1 g of $PCl_5$ and continue stirring at −78° C. for 1 h more. Warm the mixture to −60° C. and stir for another 1 h. Gradually warm the mixture to −50° C. while stirring for 3 h, then isolate the product as described in Example 2 to provide the title compound as a 93.5:6.5 mixture of $\Delta^{9,11}$ and $\Delta^{11,12}$ steroids, respectively.

EXAMPLE 4

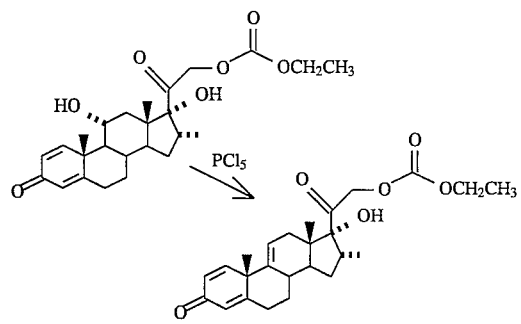

Treat a solution of 11-α-hydroxy-16-α-methyl steroid of Preparation 1B in 20 mL of THF, with 2 g of $PCl_5$ according to substantially the same procedure as described for Example 2 to provide the title compound (94% overall molar yield from starting trihydroxy steroid used in Preparation 1B). The ratio of $\Delta^{9,11}$ to $\Delta^{11,12}$ steroid is 99:1.

EXAMPLE 5

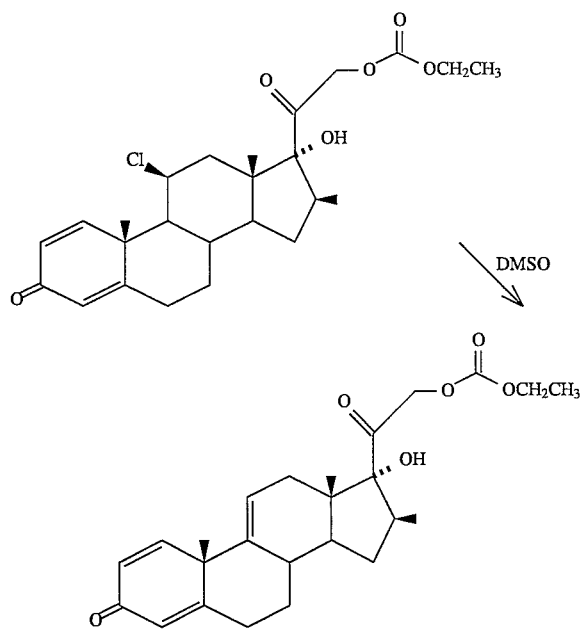

Combine 0.095 g of 11-β-chloro-17-α-hydroxy-16-β-methyl-21-ethoxycarbonyloxy-pregna- 1,4-diene-3,20-dione and a mixture of 2 mL of DMSO. Heat the mixture at 90° C. for 160 h. to form the triene product. The reaction is monitored by HPLC (μ-Bondapak® C-18 column, 1:1 $CH_3CN/H_2O$, 1.7 mL/min). The starting compound (retention time 15.5–15.6 min.) is gradually converted to the triene product (retention time 10.47 min.) over the course of the reaction. The triene is formed in >97% yield as determined by HPLC (as described above). Essentially no $\Delta^{11,12}$ steroid is formed.

Following substantially the same procedure, the results tabulated below were obtained using the solvents indicated:

| Solvent | Reaction Temp. | Reaction Time | Comments |
| --- | --- | --- | --- |
| DMSO | 110° C. | 40 min | rxn. complete |
| EtOAc/pyridine | reflux | 24 h | no reaction |
| $CHCl_3$/DBU | reflux | 24 h | no reaction |
| $THF/H_2O$ | reflux | 3 h | no reaction |
| $CH_3CN$ | reflux | 3 h | no reaction |
| $CH_3CN/H_2O$ | reflux | 8 h | rxn. complete |
| $HOAc/H_2O$ | 110° C. | 40 min | rxn. complete |
| dioxane/$H_2O$ | 100° C. | 3.5 h | rxn. complete |
| DMF | 100° C. | 5 h | rxn. complete |
| diglyme | 100° C. | 2 h | no reaction |
| diglyme | 150° C. | 2 h | 3% conversion |
| diglyme/$H_2O$ | 100° C. | <1 h | rxn. complete |

EXAMPLE 6

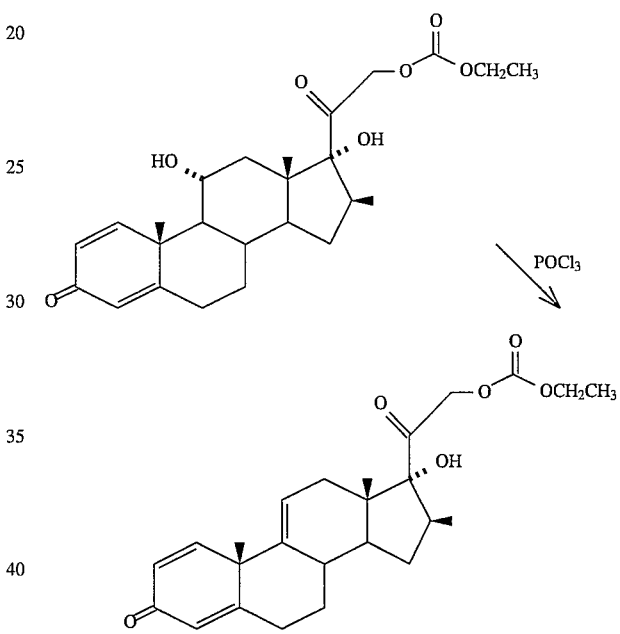

Combine 2 g of the 11-α-hydroxy steroid (isolated from the product solution of Preparation 1), 20 mL of $CH_2Cl_2$ and 5 mL of pyridine and cool to –5° C. Slowly add (dropwise) 0.84 mL (2 equivalent) of $POCl_3$ and stir at room temperature for 24 h. Add 10 mL of pyridine and stir the mixture at 60° C. for 20 h, and analyze by HPLC. The ratio of $\Delta^{9,11}$ to $\Delta^{11,12}$ is 98:2, and the solution yield is 13%.

EXAMPLE 7

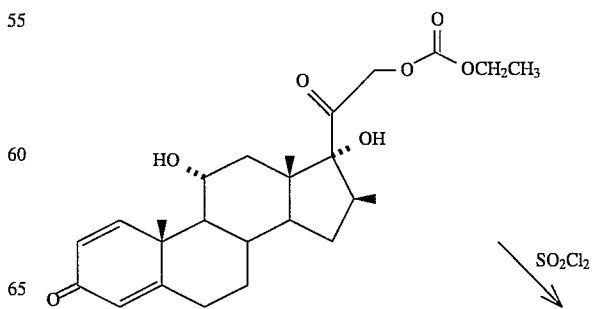

15
-continued

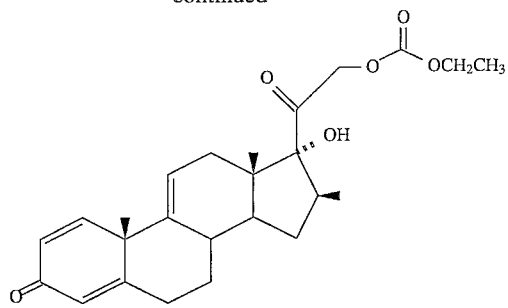

Combine 2 g of the 11-α-hydroxy steroid (isolated from the product solution of Preparation 1), 20 mL of THF and cool to −73° C. Add 0.5 mL (1.4 equivalents) of $SO_2Cl_2$, stir for 20 min., then add 1.2 g of imidazole (4 equivalents). Stir the mixture for 1 h., then analyze by HPLC. The ratio of $\Delta^{9,11}$ to $\Delta^{11,12}$ is 92.8:7.2.

EXAMPLE 8

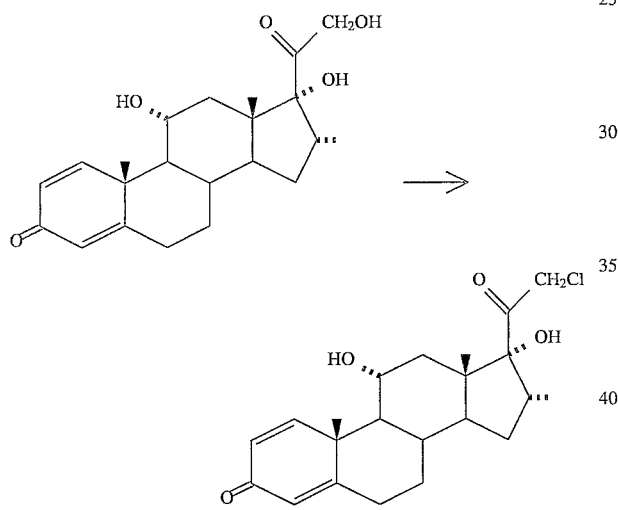

Combine 1 g of 16α-methyl-11α,17α, 21-trihydroxypregna-1,4-diene-3,20-dione, 0.73 g of $PPh_3$, 5 mL of $CCl_4$ and 5 mL of $CH_3CN$, and stir the mixture at room temperature for 1 h. Add 0.25 g of $PPh_3$, stir 20 min. more. Analyze by HPLC to determine the extent of reaction. The product 21-chloride is 98% pure by HPLC.

EXAMPLE 9

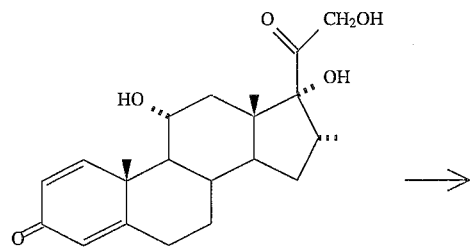

16
-continued

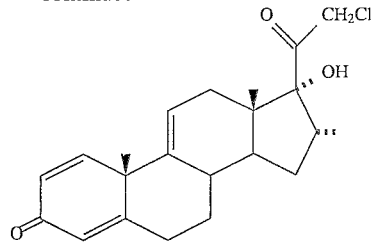

Combine 2.03 g of 16α-methyl-11α,17α, 21-trihydroxypregna-1,4-diene-3,20-dione, 4.01 g of $PPh_3$, 6 mL of $CCl_4$ and 12 mL of $CH_3CN$, and stir the mixture at room temperature for 3 h. Heat the mixture at reflux overnight then analyze by HPLC to determine the extent of reaction. HPLC shows a 74% solution yield of the triene product.

EXAMPLE 10

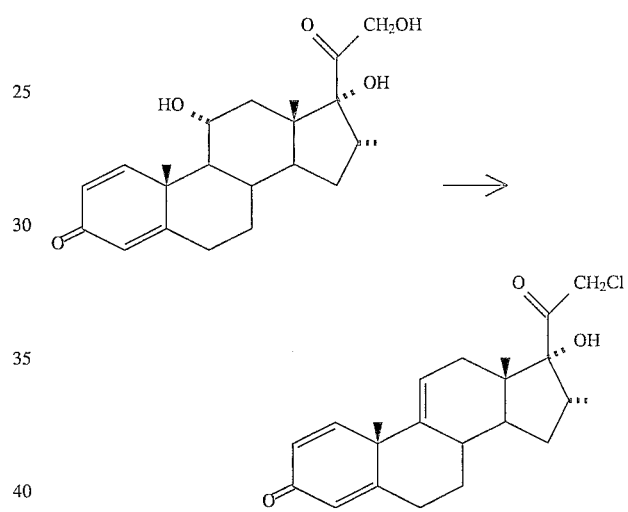

Combine 2 g of 16α-methyl-11α,17α, 21-trihydroxypregna-1,4-diene-3,20-dione, 1.05 g of imidazole, 15 mL of $CH_2Cl_2$ and cool the mixture to −20° C. Add 0.45 mL of $SO_2Cl_2$ and stir the mixture while monitoring by HPLC. Add water to quench the mixture, extract with $CH_2Cl_2$. Wash the organic extract with $NaHCO_3$ (aqueous), then with water, and dry over $Na_2SO_4$. Concentrate in vacuo to give the triene product (50% molar yield).

EXAMPLE 11

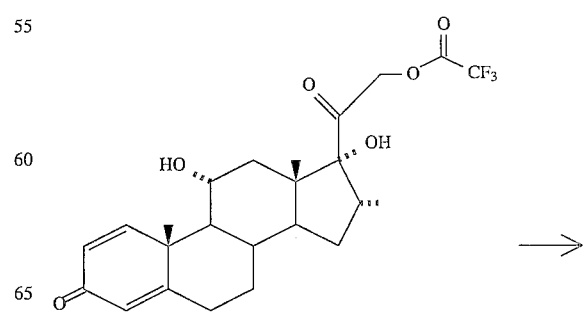

17
-continued

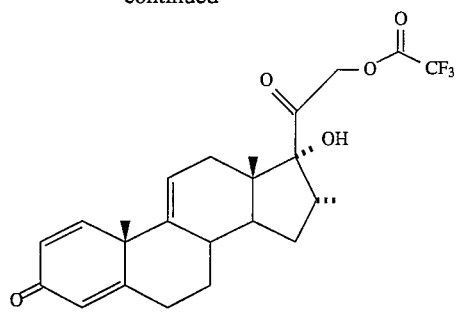

Cool the product solution from Preparation 4 to −78° C., add 2 g of $PCl_5$ and stir the mixture at −78° C. to give a solution of the triene product. Analyze the product by HPLC. The ratio of $\Delta^{9,11}$ to $\Delta^{11,12}$ is 98.6:1.4.

EXAMPLE 12

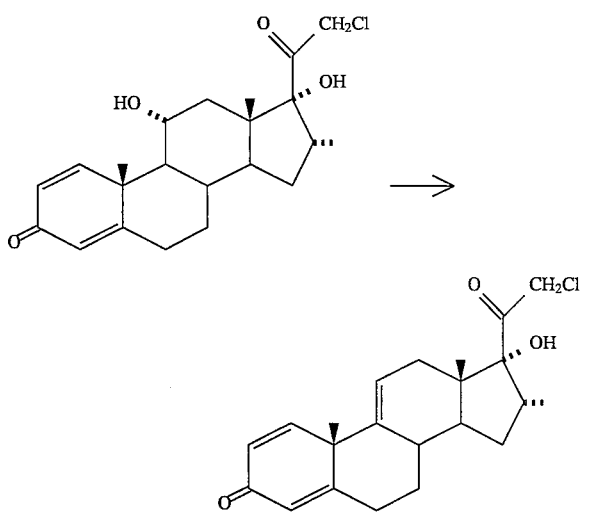

Prepare a solution 2 g of the product of Preparation 5 in 20 mL of THF. Cool the solution to −78° C., add 2 g of $PCl_5$ and stir at −78° C. for 30 min. Add 20 mL of water, extract with $CH_2Cl_2$ (2×30 mL) and wash the combined extracts with water. Dry over $Na_2SO_4$ and concentrate in vacuo to give the triene product.

EXAMPLE 13

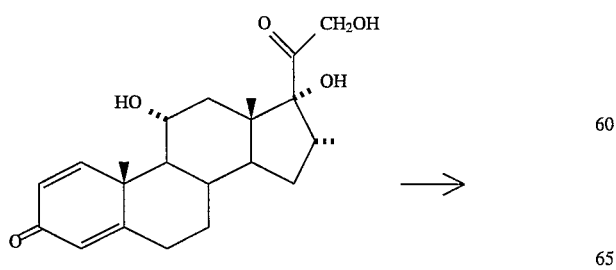

18
-continued

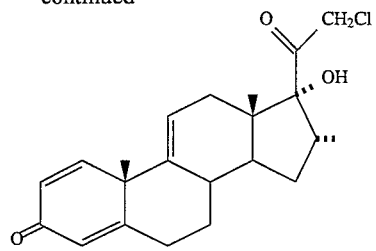

Combine 2.03 g of 16α-methyl-11α,17α, 21-trihydroxypregna-1,4-diene-3,20-dione, 16 mL of $CH_2Cl_2$, 50 mg of DMAP, 2 mL of $Et_3N$ and 1.23 g of TsCl. Stir the mixture at room temperature for about 1 h., then add 20 mL of water and adjust to pH=1 by adding HCl (aqueous). Extract with $CH_2Cl_2$ (2×20 mL), combine the extracts and concentrate in vacuo to give a residue. Add 30 mL of THF to the residue and concentrate in vacuo. Add 20 mL of THF and 2.1 g of $Li_2CO_3$, cool to −78° C. and add 2 g of $PCl_5$. Stir the mixture at −78° C. for 30 min., add 1 g of $Li_2CO_3$, and warm to room temperature. Add 0.5 g of $Li_2CO_3$ and stir the mixture overnight at room temp. Filter and add $CH_2Cl_2$ and THF to bring the filtrate volume to 250 mL to give a solution of the product triene. The solution yield is 84.7% as determined by HPLC.

The reaction can also be run using about 3 g of $Li_2CO_3$, which can be added in portions as described or can be added all at once prior to the addition of $PCl_5$.

EXAMPLE 14

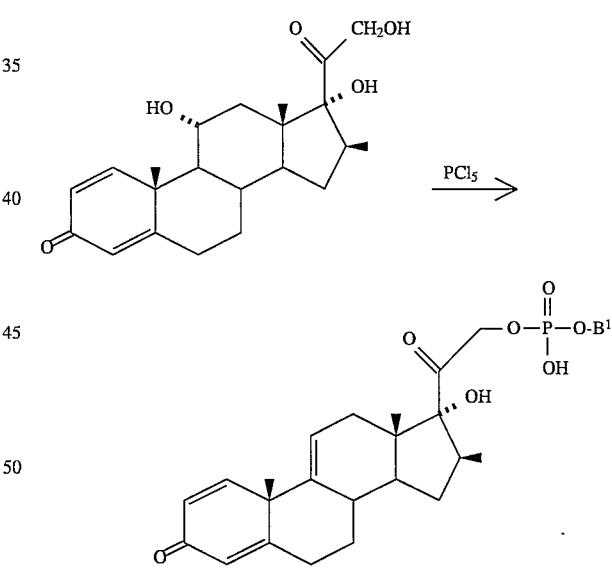

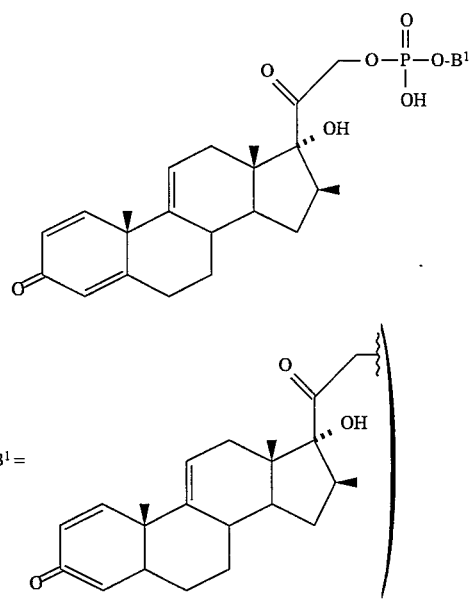

Combine 2 g of 16β-methyl-11α,17α, 21-trihydroxypregna-1,4-diene-3,20-dione and 20 mL of THF and cool to −78° C. Add 2 g of PCl and stir for 20 min at −78° C. Pour the mixture into water, filter and wash the solids with water to give the phosphate dimer product. FAB MS: 775 (M$^+$+1); FAB MS (NaCl): 797 (M+Na$^+$).

We claim:

1. A regioselective process for preparing $\Delta^{9,11}$ steroids of the formula

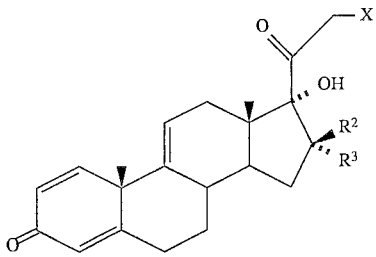

wherein one of $R^2$ or $R^3$ is $CH_3$ and the other is H; and X is H, halogeno or —OR, wherein R is H or —C(O)R$^1$, and R$^1$ is $CF_3$, $C_1$–$C_6$ alkyl or $C_1$–$C_6$ alkoxy, comprising treating an 11-α- or 11-β-hydroxy steroid of the formula

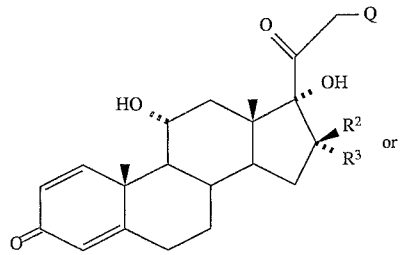

or

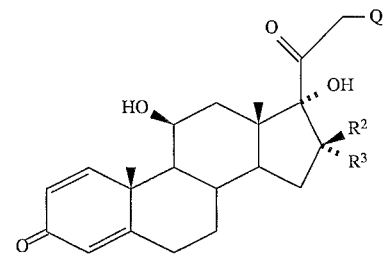

respectively, wherein Q is —OSO$_2$C$_6$H$_4$CH$_3$, —OSO$_2$CH$_3$, —O—C(O)O—B or X, wherein B is a group of the formula

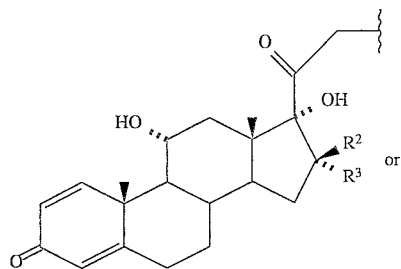

or

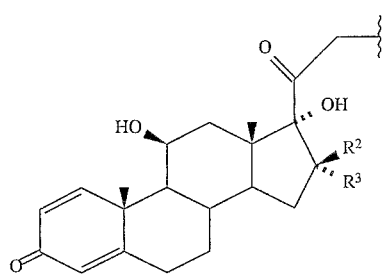

and wherein X, R$^2$ and R$^3$ are as defined above, with PCl$_5$, PCl$_3$, POCl$_3$ or either SO$_2$Cl$_2$ and imidazole, or triphenylphosphine and CCl$_4$.

2. The process of claim 1 wherein the steroid is prepared using PCl$_5$.

3. The process of claim 2 wherein treatment is carried out in the presence of tetrahydrofuran at a temperature of 0° to −100° C.

4. The process of claim 3 wherein the temperature is −40° C. to −90° C.

5. The process of claim 4 wherein the temperature is −60° to −85° C.

* * * * *